(12) United States Patent
Smith

(10) Patent No.: US 12,257,395 B1
(45) Date of Patent: Mar. 25, 2025

(54) OXYGEN TUBING BOX AND METHOD OF USE

(71) Applicant: Diane M. Smith, Southlake, TX (US)

(72) Inventor: Diane M. Smith, Southlake, TX (US)

( * ) Notice: Subject to any disclaimer, the term of this patent is extended or adjusted under 35 U.S.C. 154(b) by 342 days.

(21) Appl. No.: 17/459,329

(22) Filed: Aug. 27, 2021

Related U.S. Application Data

(60) Provisional application No. 63/140,472, filed on Jan. 22, 2021.

(51) Int. Cl.
  *A61M 25/00* (2006.01)
  *A61M 16/08* (2006.01)

(52) U.S. Cl.
  CPC ...... *A61M 25/002* (2013.01); *A61M 16/0875* (2013.01); *A61M 2205/3368* (2013.01); *A61M 2205/36* (2013.01)

(58) Field of Classification Search
  CPC ...... H05B 6/105; B29B 13/024; B23K 3/063; Y10S 242/916
  See application file for complete search history.

(56) References Cited

U.S. PATENT DOCUMENTS

| | | | | |
|---|---|---|---|---|
| 4,944,464 A | * | 7/1990 | Zelenka | B23K 3/063 226/188 |
| 4,987,827 A | * | 1/1991 | Marquez | A47J 37/0611 99/425 |
| 9,146,042 B1 | * | 9/2015 | Kurosu | B29C 35/045 |
| 2003/0226581 A1 | * | 12/2003 | Peele | A45D 27/46 134/201 |

FOREIGN PATENT DOCUMENTS

CN  109893722 A  * 6/2019

* cited by examiner

*Primary Examiner* — Thien S Tran
(74) *Attorney, Agent, or Firm* — Richard Eldredge; Leavitt Eldredge Law Firm

(57) ABSTRACT

An oxygen tubing box includes a box having a lid attached to a body forming an interior cavity; a channel extending through a portion of the interior cavity exiting to an exterior of the box, the channel to receive an end of oxygen tubing; a spindle positioned within the interior cavity and to connect to the channel; one or more pulleys positioned within the interior cavity along the channel; a control panel housed within the interior cavity, the control panel having a power source to provide power to the box; and a heater configured to heat the interior cavity of the box; a motor connected to the one or more pulleys; operation of the motor is to rotate the one or more pulleys; and the heater provides heat to relax the oxygen tubing.

5 Claims, 5 Drawing Sheets

OXYGEN TUBING BOX AND METHOD OF USE

BACKGROUND

1. Field of the Invention

The present invention relates generally to oxygen delivery systems, and more specifically, to a system that will improve and enhance the delivery of oxygen by means of using existing in-home oxygen concentrator units by improving the functionality of using the existing plastic oxygen tubing for home use today, using a method that will keep the tubing from twisting, kinking and eventually cutting off oxygen flow.

2. Description of Related Art

It has been estimated that more than 250 million people in the world may have Chronic Obstructive Pulmonary Disease (COPD), and over 65 million of these cases are moderate to severe. Some experts think that the number of individuals with COPD may be even higher than expected, both around the world and in the United States (US).

Everyone on home oxygen with longer oxygen tubing (25 ft plus) deals with the constant kinking, twisting and lack of oxygen flow associated with the home concentrator oxygen tubing. Kinked and twisted oxygen tubing is dangerous to the oxygen user, and it is a terrible nuisance. Not only is the person with the COPD suffering from the disease, but they are also fighting their equipment to properly deliver the oxygen.

Accordingly, although great strides have been made in the area of oxygen delivery systems, shortcoming still remain.

It is an object of the present invention to provide a solution to the aforementioned problems.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
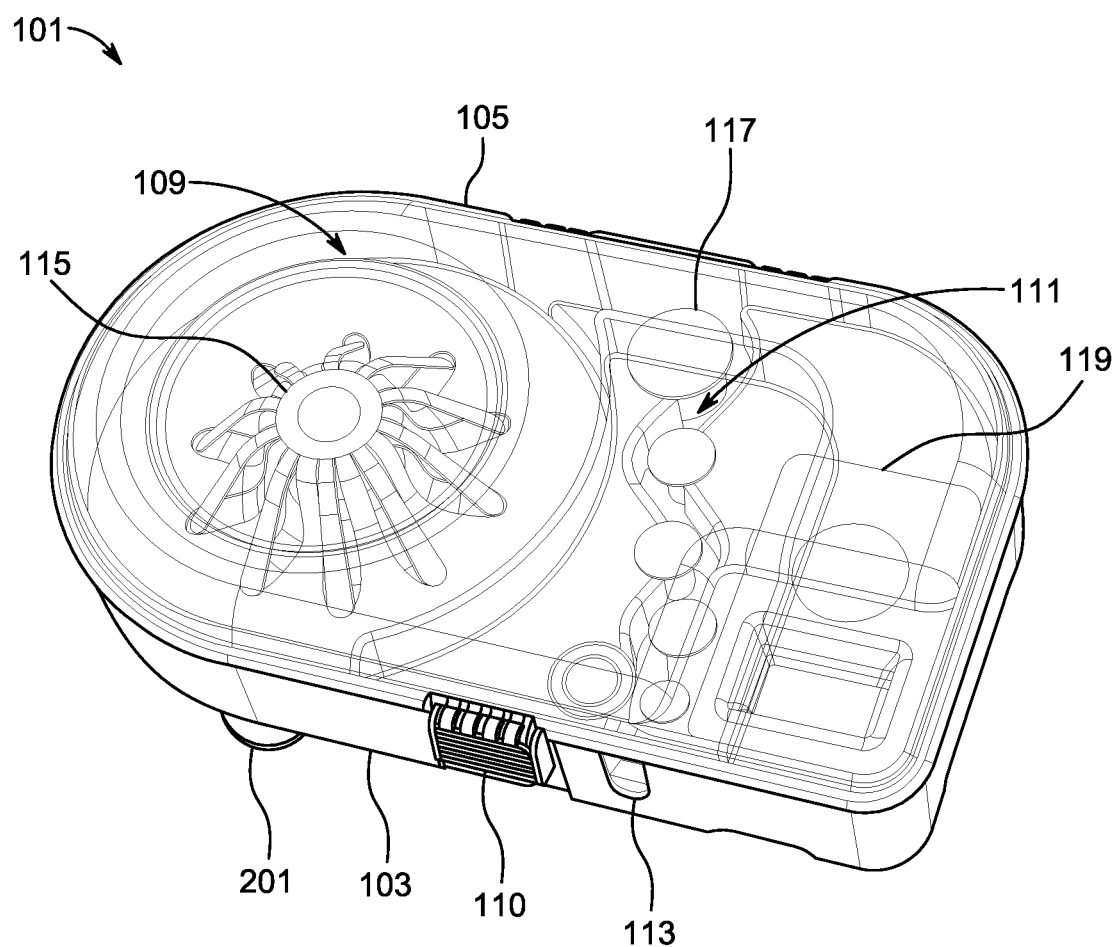
FIG. 1 is a top isometric view of a oxygen tubing box in accordance with the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional oxygen delivery systems. Specifically, the present invention provides for a system that aids in reducing kinks associated with conventional oxygen delivery systems. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a top isometric view of an oxygen tubing box 101 in accordance with a preferred embodiment of the present application. It will be appreciated that box 101 overcomes one or more of the above-listed problems commonly associated with conventional oxygen tubing systems.

In the contemplated embodiment, box 101 includes a body 103 having a lid 105 attached to the body forming an interior cavity 109. The interior cavity is configured to receive oxygen tubing, as will be discussed herein. The lid may be clear to allow visibility into the box, or alternatively may be colored to prevent visibility. The lid may be completely removable or attached via hinges and can secure via a latch 110 to lock the lid in place.

The box 101 further includes a channel 111 extending through a portion of the interior cavity exiting through an opening 113 to an exterior of the box. The channel 111 configured to receive an end of oxygen tubing. As further shown, a spindle 115 is positioned within the interior cavity 109 and is configured to connect to the channel 111. One or more pulleys 117 are also positioned within the interior cavity along the channel 111. A control panel 119 is also housed within the interior cavity.

Figure 3:
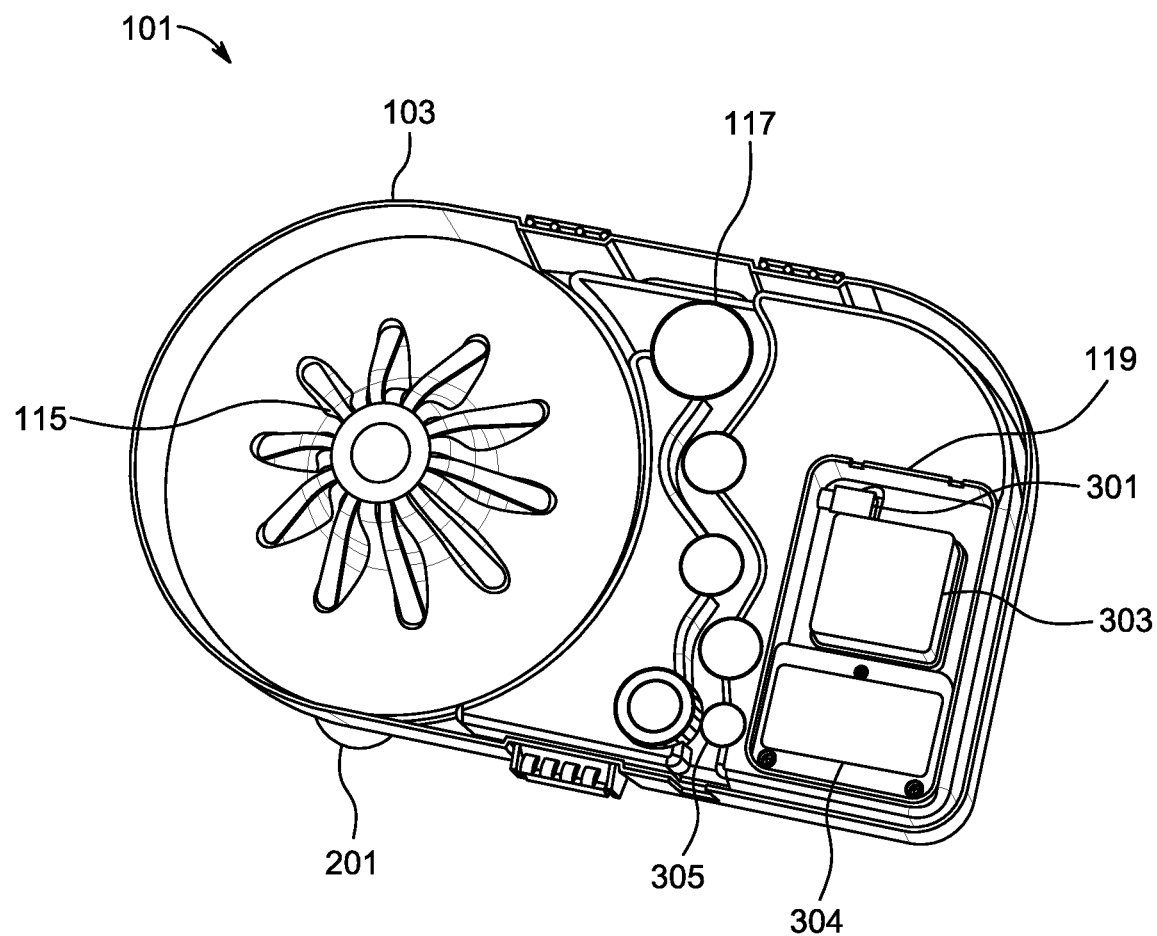
FIG. 3 is a top isometric view of the oxygen tubing box of FIG. 1 with the top removed in accordance with the present application.
Figure 4:
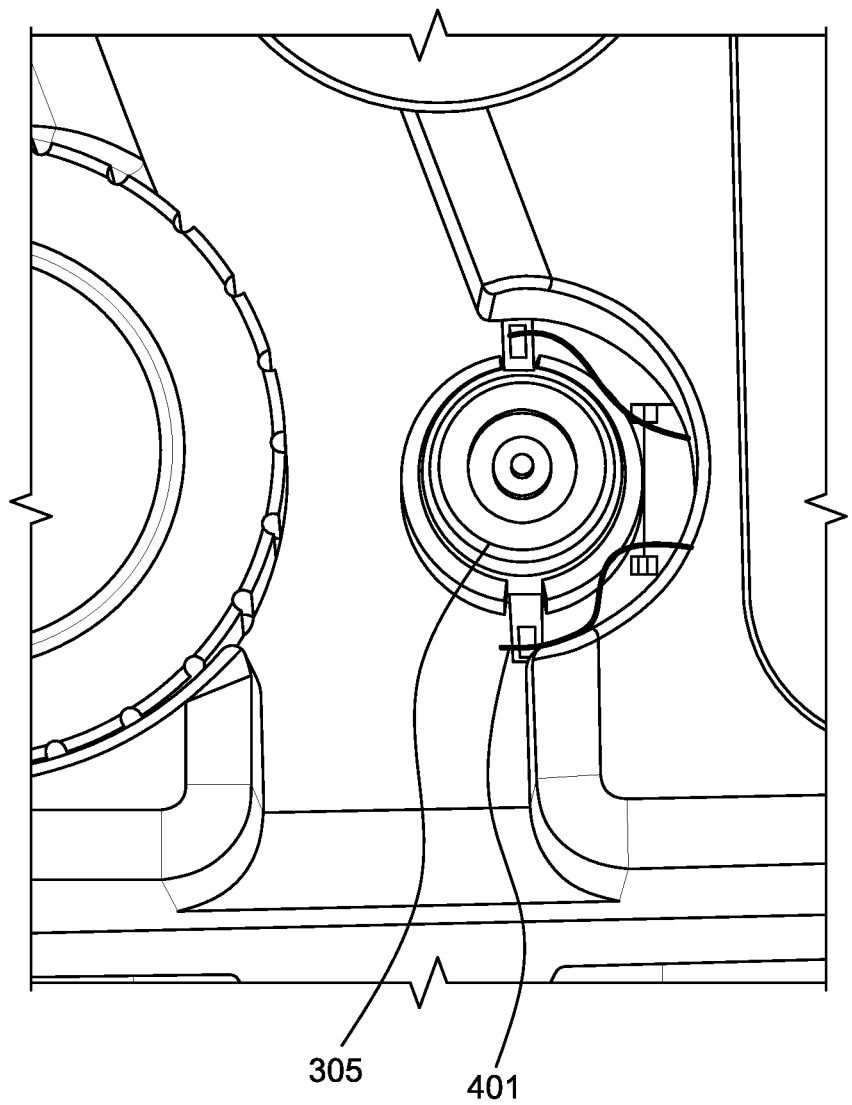
FIG. 4 is a close up showing a motor of the oxygen tubing box in accordance with the present application.

As better shown in FIG. 3, the control panel 119 has a power source 301 configured to provide power to the box 101, a heater 303 configured to heat the interior cavity of the box 101, and a temperature controller 304. The temperature controller may include an LED display and various controls to allow for user operation. The heater 303 may incorporate a fan to allow for heating of the interior area. A motor 305 is connected to the one or more pulleys 117 and connected to the control panel via one or more wires 401 (shown in FIG. 4), wherein operation of the motor is configured to rotate the one or more pulleys. During operation, the heater 303 provides heat to heat up and relax the oxygen tubing when the tubing is within the box. Once the tubing is hot enough after several minutes the tubing is pulled through the pulleys until all of the tubing is pulled through the box and the tubing is flattened and 're-memorized' so that it will no longer twist and kink for the pulmonary doctor's recommended two (2) month period.

It should be appreciated that the power source 301 can vary as would be known in the art, such as being battery powered or configured to plug into a 110 outlet. Further, it should be appreciated that the overall aesthetics of the box can vary, such as having varying shapes and details.

Figure 2:
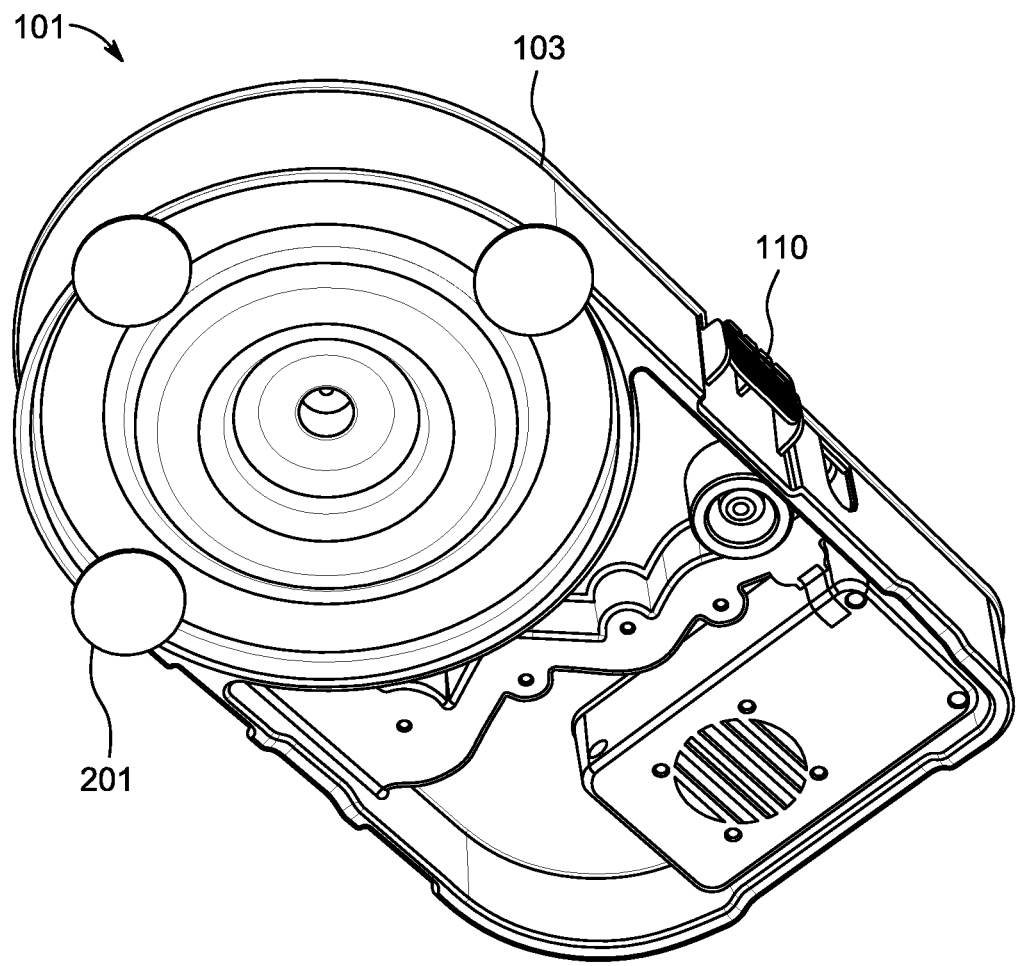
FIG. 2 is a bottom isometric view of the oxygen tubing box of FIG. 1 in accordance with the present application.

As shown in FIG. 2, the box 101 may include one or more suction cups 201 which allow for securement of the box to a surface. This allows for the box to remain stable while in operation.

It should be appreciated that one of the unique features believed characteristic of the present application is the configuration of the box that allows for tubing to extend through the channel, wherein the tubing is heated via the heater. This allows for the tubing to relax such that kinking and twisting of the tubing is reduced when in use. This allows for safer and more efficient operation of oxygen tubing by the end user.

Figure 5:
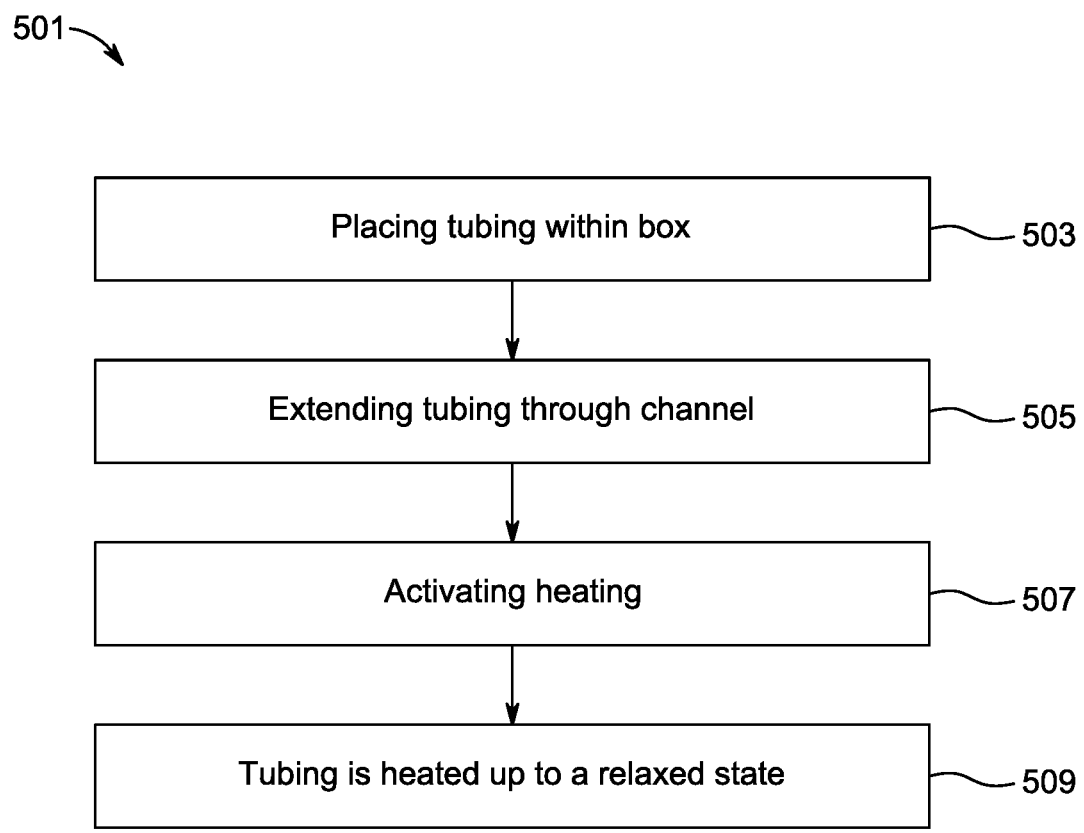
FIG. 5 is a flowchart of a method of use of the oxygen tubing box in accordance with the present application.

In FIG. 5, a flowchart 501 depicts a method of use of box 101. During use, the user will insert the tubing within the box and extend an end of the tubing through the channel to exit the opening, as shown with boxes 503, 505. The user will then activate heating of the box via the temperature controller and the heater, as shown with box 507. The tubing can then be heated and pulled through the box such that the tubing is reduced in kinks, as shown with box 509.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An oxygen tubing box comprises:
    a body having a lid attached to the body forming an interior cavity;
    a channel extending through a portion of the interior cavity exiting to an exterior of the box, the channel configured to receive an end of oxygen tubing of an elongated oxygen tube;
    a spindle positioned within the interior cavity and configured to connect to the channel;
    one or more pulleys positioned within the interior cavity along the channel, the one or more pulleys are configured to engage with the elongated oxygen tube, the one or more pulleys direct the elongated tube within the channel;
    a control panel housed within the interior cavity, the control panel having:
        a power source configured to provide power to the box; and
        a heater configured to heat the interior cavity of the box and configured to heat the elongated tube while the elongated tube is within the channel, the heater is positioned adjacent to the channel and heat from the heater is directed towards the channel to heat the end of the oxygen tubing;
    a motor connected to the one or more pulleys, the motor is configured to move the end of the oxygen tubing within the channel;
    wherein operation of the motor is configured to rotate the one or more pulleys; and
    wherein the heater provides heat to relax the oxygen tubing.

2. The oxygen tubing box of claim 1, further comprising: one or more suction cups positioned on a bottom surface of the body.

3. The oxygen tubing box of claim 1, wherein the control panel further includes an LED temperature controller configured to operate the heater.

4. The oxygen tubing box of claim 1, wherein the heater includes a fan.

5. The oxygen tubing box of claim 1, wherein the lid secures in a closed position with the body via a latch.

* * * * *